(12) United States Patent
Sherr (10) Patent No.: US 11,957,655 B2
(45) Date of Patent: Apr. 16, 2024

(54) METHODS OF TREATING HEARING LOSS

(71) Applicant: The Regents of the University of California, Oakland, CA (US)

(72) Inventor: Elliott Sherr, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/771,195

(22) PCT Filed: Oct. 22, 2016

(86) PCT No.: PCT/US2016/058348
§ 371 (c)(1),
(2) Date: Apr. 26, 2018

(87) PCT Pub. No.: WO2017/074830
PCT Pub. Date: May 4, 2017

(65) Prior Publication Data
US 2018/0311207 A1    Nov. 1, 2018

Related U.S. Application Data

(60) Provisional application No. 62/246,425, filed on Oct. 26, 2015.

(51) Int. Cl.
| | |
|---|---|
| *A61K 31/165* | (2006.01) |
| *A61K 31/045* | (2006.01) |
| *A61K 31/05* | (2006.01) |
| *A61K 31/167* | (2006.01) |
| *A61K 31/365* | (2006.01) |
| *A61K 31/381* | (2006.01) |
| *A61K 31/404* | (2006.01) |
| *A61K 31/4706* | (2006.01) |
| *A61K 31/496* | (2006.01) |
| *A61K 31/519* | (2006.01) |
| *A61K 31/52* | (2006.01) |
| *A61K 31/5415* | (2006.01) |
| *A61K 31/69* | (2006.01) |
| *A61K 31/7076* | (2006.01) |
| *A61P 27/16* | (2006.01) |

(52) U.S. Cl.
CPC .......... *A61K 31/365* (2013.01); *A61K 31/045* (2013.01); *A61K 31/05* (2013.01); *A61K 31/165* (2013.01); *A61K 31/167* (2013.01); *A61K 31/381* (2013.01); *A61K 31/404* (2013.01); *A61K 31/4706* (2013.01); *A61K 31/496* (2013.01); *A61K 31/52* (2013.01); *A61K 31/5415* (2013.01); *A61K 31/69* (2013.01); *A61K 31/7076* (2013.01); *A61P 27/16* (2018.01)

(58) Field of Classification Search
CPC ... C07C 235/14; C07C 211/29; C07C 235/20; C07C 235/22; C07C 235/24; C07C 255/54; C07C 257/14; C07C 271/24; C07C 271/52; C07C 317/22; C07C 317/44; C07C 323/60; A61K 31/165; A61K 31/4192; A61K 31/365; A61K 31/045; A61K 31/05; A61K 31/167; A61K 31/381; A61K 31/404; A61K 31/4706; A61K 31/496; A61K 31/52; A61K 31/5415; A61K 31/69; A61K 31/7076; A61K 31/519; A61P 27/16

See application file for complete search history.

(56) References Cited

FOREIGN PATENT DOCUMENTS

WO    WO2014/144952    *    9/2014    .......... A61K 31/165

OTHER PUBLICATIONS

Hetz et al. Nature Chemical Biology 2019, 15, 764-775.*
Oishi et al. Cell Death and Disease 2015, 6, e1763, p. 1-11, published on line May 14, 2015.*
Wang et al. J. Otorhinolaryngol. Hear. Balance Med. 2018, 1, 3, p. 1-12.*
Prasad V et al: "Phenotypes of SERCA and PMCA knockout mice", Biochemical and Biophysical Research Communications. Elsevier. Amsterdam. Nl, vol. 322. No. 4, Oct. 1, 2004 (Oct. 1, 2004). pp. 1192-1203. XP004536604, ISSN: 0006-291X. DOI:10.1016/J.BBRC.2004.07.156, paragraph: PMCA2.
Wang Wenwen et al: "Impaired unfolded protein response in the degeneration of cochlea cells in a mouse model of age-related hearing loss", Experimental Gerontology. Elsevier. Amsterdam. NL. vol. 70. Jul. 12, 2015 (Jul. 12, 2015). pp. 61-70. XP029291149, ISSN: 0531-5565. DOI:10.1016/J.EXGER.2015.07.003; abstract; 1-16, paragraph [04.1].
P Garcia-Huerta et al: "Stressing out the ER in aminoglycoside-induced hearing loss", Cell Death & Disease, vol. 6. No. 5. May 1, 2015 (May 1, 2015), pp. e1762-e1762. XP55589044. DOI: 10.1038/cddis.2015.133 * the whole document *.
Scheffer, D. I. et al., 'Gene expression by mouse inner ear hair cells 34-37during development' The Journal of Neuroscience, Apr. 2015, vol. 35, No. 16, pp. 6366-6380. See abstract; and table 1.

(Continued)

*Primary Examiner* — Irina Neagu
(74) *Attorney, Agent, or Firm* — MARSHALL, GERSTEIN & BORUN LLP (57) ABSTRACT

Provided are methods of treating various forms of hearing loss caused by aberrant calcium fluxes in auditory cells. The methods encompass the administration of agents which prevent abnormal calcium fluxes, stabilize SERCA2b activity, or prevent ER UPR apoptotic responses. The methods include therapeutic treatments of subjects suffering from hearing loss as well as preventative treatments which protect auditory cells from cell death, for example as caused by exposure to loud noise.

10 Claims, 4 Drawing Sheets

(56) References Cited

OTHER PUBLICATIONS

Ben-Yosef, T. et al., Claudin 14 knockout mice, a model for autosomal 34-37 recessive deafness DFNB29, are deaf due to cochlear hair cell degeneration, Human Molecular Genetics, 2003, vol. 12, No. 16, pp. 2049-2061. See abstract; pp. 2050-2053; and figure 1.
Masuda, M. et al., Correlations of inflammatory biomarkers with the onset 34-37,39,40 and prognosis of idiopathic sudden sensorineural hearing loss, Otology & Neurotology, 2012, vol. 33, pp. 1142-1150. See the whole document.
Ohlemiller, K. K. Contributions of mouse models to understanding of 34-37,39,40 age-and noise-related hearing loss, Brain Research, 2006, vol. 1091, pp. 89-102. See the whole document.
Johnson, K. R. et al., 'A major gene affecting age-related hearing loss in C57BL/6J mice' Hearing research, 1997, vol. 114, pp. 83-92. See the whole document.
Li et al., 2018. Deletion of Tmtc4 activates the unfolded protein response and causes postnatal hearing loss, J Clin Invest. 128: 5150-5162.
LeBeau et al., 2018, The PERK Arm of the Unfolded Protein Response Regulates Mitochondrial Morphology during Acute Endoplasmic Reticulum Stress, Cell Reports 22:2827-2836.
Romine and Wiseman, 2019. PERK Signaling Regulates Extracellular Proteostasis of an Amyloidogenic Protein During Endoplasmic Reticulum Stress, Scientific Reports 9: 410.
Radford et al., 2015. PERK inhibition prevents tau-mediated neurodegeneration in a mouse model of frontotemporal dementia Acta Neuropathologica 130: 633-642.
Wang et al., 2020. PERK Inhibition Promotes Post-angioplasty Re-endothelialization via Modulating SMC Phenotype Changes, J Surg Res 257: 294-305.
Szegezdi et al., 2003, Caspase 12 and ER Stress Mediated Apoptosis—the story so far, Ann New York Acad Sci. 1010:186-194.
Fujimoto and Yamasoba, 2014, Oxidative Stresses and Mitochondrial Dysfunction in Age-Related Hearing Loss, Oxid Med Cell Longev. 2014:582849.
Melgar-Rojas et al., 2015. Cellular Mechanisms of Age-Related Hearing Loss, Chapter 15, Free Radicals in ENT Pathology, pp. 305-333.
Furness, 2015, Molecular basis of hair cell loss, Cell Tissue Res (2015) 361:387-399.
Ceriani et al., "Calcium Signaling in the Cochlea—Molecular Mechanisms and Physiopathological Implications", *Cell Commun Signal,* vol. 10, p. 20, published online Jul. 12, 2012.

Gruber et al., "Discovery of enzyme modulators via high-throughput time resolved FRET in living cells", *J. Biomolecular Screening,* vol. 19, No. 2, pp. 215-222, Jan. 16, 2014.
Hetz et al., "Targeting the unfolded protein response in disease", *Nature Reviews: Drug Discovery,* vol. 12, pp. 703-712 Sep. 2013.
Rybak et al., Mechanisms of cisplatin-induced ototoxicity and prevention, Hearing research, vol. 226, pp. 157-167, Nov. 17, 2006.
Watanabe K-I et al., "Nitric oxide synthase inhibitor suppresses the ototoxic side effect of cisplatin in guinea pigs", Anti-Cancer Drugs, vol. 11, No. 5, pp. 401-406, Jun. 2000.
Cai et al. 2019. Metformin attenuates the D-galactose-induced aging process via the UPR through the AMPK/ERK1/2 signaling pathways. Int. J Mol. Med. 45: 715-730. Published Jan. 28, 2020.
Hu et al., 2016. ER stress inhibitor attenuates hearing loss and hair cell death in Cdh23erl/erl mutant mice. Cell Death and Disease (2016) 7, e2485; doi:10.1038/cddis.2016.386.Published Feb. 6, 2020.
Li et al., 2019. Chemical chaperone 4-phenylbutyrate prevents hearing loss and cochlear hair cell death in Cdh23erl/erl mutant mice. Neuroreport. Feb. 6, 2019; 30(3): 145-150. Published Feb. 6, 2019.
Jia et al., 2020. Glucocorticoid-induced leucine zipper protects noise-induced apoptosis in cochlear cells by inhibiting endoplasmic reticulum stress in rats. Medical Molecular Morphology (2020) 53:73-81. Published Sep. 4, 2019.
Zong et al., 2017. Endoplasmic Reticulum Stress Is Involved in Cochlear Cell Apoptosis in a Cisplatin-Induced Ototoxicity Rat Model. Audiol Neurotol 2017;22:160-168. Published Oct. 20, 2017.
Wen et al., 2021 [Abstract] Tauroursodeoxycholic acid attenuates cisplatin-induced ototoxicity by inhibiting the accumulation and aggregation of unfolded or misfolded proteins in the endoplasmic reticulum. Published Apr. 15, 2021.
Liu et al., 2021. Glucocorticoids protect HEI-OC1 cells from tunicamycin-induced cell damage via inhibiting endoplasmic reticulum stress. Open Life Sciences 2021; 16: 695-702. Published Jul. 1, 2021.
Lu et al., 2022. Salubrinal Protects Against Cisplatin-Induced Cochlear Hair Cell Endoplasmic Reticulum Stress by Regulating Eukaryotic Translation Initiation Factor $2\alpha$ Signalling. Front. Mol. Neurosci. 30: doi :10.3389/fnmol.2022.916458. Published May 30, 2022.
Lee et al., 2021. Heat Shock Factor 1 Prevents Age-Related Hearing Loss by Decreasing Endoplasmic Reticulum Stress. Cells 10: 2454. Published Sep. 17, 2021.
Hetz et al., "The unfolded protein response: controlling cell fate decisions under ER stress and beyond," Molecular Cell Biology, 13:89-102 (2012).

* cited by examiner

METHODS OF TREATING HEARING LOSS

CROSS-REFERENCE TO RELATED APPLICATIONS

This application claims priority to International Application No. PCT/US2016/058348, entitled "NOVEL METHODS OF TREATING HEARING LOSS," filed on Oct. 22, 2016, which claims priority to U.S. Provisional Application No. 62/246,425, entitled "NOVEL METHODS OF TREATING HEARING," filed on Oct. 26, 2015, each of which is incorporated by reference herein in its entirety.

STATEMENT REGARDING FEDERALLY SPONSORED RESEARCH OR DEVELOPMENT

This invention was made with government support under grant no. R01 NS058721 awarded by the National Institutes of Health. The government has certain rights in the invention.

BACKGROUND OF THE INVENTION

Hearing loss is a significant public health concern. The overall prevalence is 10.5% of the male population and 6.8% of females. Therefore, about thirty million Americans have bilateral hearing loss, based on standard hearing examinations. 18% of adults 45-64 years old, 30% of adults 65-74 years old and 47% of adults 75 years or older have hearing loss. A full 27% of hearing loss occurs in an acute setting (ear infection, ear injury and loud brief noise), while another 23% occur from more chronic exposure to sound. The NICHD estimates that 26 million Americans between the ages of 20 and 69 have high frequency hearing loss due to exposure at work or during leisure activities. Thus, there is with this group alone a very significant population in the US who could benefit immediately from treatments that can prevent these exposure-based hearing loss cases. There are also genetic contributions to hearing loss, with 3 out of 1,000 births associated with detectable hearing impairment. The costs of hearing loss to society are also significant, for example, the average lifetime expenses for a person with prelingual significant hearing impairment average about one million dollars.

SUMMARY OF THE INVENTION

Advantageously, the inventor of the present disclosure has discovered that the death of hair cells in the ear can be caused by over-activation of the unfolded protein response. Specifically, the action of dysregulated calcium fluxes has been implicated in the death of hair cells, which dysregulated calcium fluxes result in over-activation of apoptotic UPR processes. Accordingly, in one aspect, the scope of the invention encompasses treatments which inhibit or reverse abnormal calcium fluxes that trigger maladaptive UPR pathways in auditory cells, including hair cells and supporting cells of the cochlea. In another aspect, the invention is directed to treatments that inhibit maladaptive UPR pathways in order to rescue hair cells from cell death. The scope of the invention encompasses therapeutic treatments for subjects suffering from various forms of hearing loss, and further encompasses preventative treatments for subjects at risk of hearing damage.

DETAILED DESCRIPTION OF THE INVENTION

The invention encompasses various methods of treating a hearing loss condition in an animal subject. As used herein, "treatment" of a hearing loss condition means the administration of one or more chemical or biological agents to the animal subject in order to: alleviate causative processes underlying the hearing loss; reduce one or more symptoms or measures of hearing loss; prevent, ameliorate, inhibit, or reverse the loss of hair cells; and/or otherwise inhibit processes that negatively affect auditory ability.

Some of the treatments described herein are directed to the modulation of a target enzyme, process, or the like. As used herein, "modulate" means to act by an agent to regulate, to control or to change the activity of the target, including enhancement of the target.

A "hearing loss condition," as used herein, broadly encompasses any damage to the auditory systems, organs, and cells or any impairment of an animal subject's ability to hear sound, as measured by standard methods and assessments known in the art, for example optoacoustic emission testing, pure tone testing, and auditory brainstem response testing. Exemplary hearing loss conditions include noise-induced hearing loss, resulting from chronic or acute exposure to loud noise (e.g. noise above 75 decibels), for example occupational noise such as construction noise, aircraft noise, and military noise, or recreational noise such as experienced by musicians, concert attendees, or racetrack attendees. Hearing loss conditions further include various forms of age-related hearing loss, as known in the art. Hearing loss conditions further encompass various hearing impairments resulting from genetic or inherited factors, for example, congenital hearing loss, Stickler syndrome, Waardenburg syndrome, and non-syndromic hearing loss, including hearing pathologies associated with genes such as GJB2 and GJB6. Hearing loss conditions further include hearing loss associated with disease conditions, such as ear infection, meningitis, autoimmune disease, and other conditions known in the art. Additionally, hearing loss conditions can include hearing impairment caused by acute or chronic exposure to ototoxic agents, i.e. species which damage hearing, for example such as cisplatin, gentamicin, toluene, lead, and other species known in the art. Also, hearing loss conditions include hearing impairment associated with trauma, for example, resulting from head injuries.

Hearing loss conditions also include any reduction in the function or number of auditory cells, including hair cells, cochlear cells, or supporting cells thereof. Hair cells include inner hair cells and outer hair cells. Cochlear cells include neurons of the vestibulocochlear nerve and other cells associated with the perception of sound.

In various embodiments, the treatments of the invention may encompass therapeutic treatments to alleviate a hearing loss condition in an individual animal suffering therefrom. Therapeutic treatments include those which reduce or reverse the severity of a hearing loss condition: improve the function of auditory cells, including hair cells; or which increase or preserve the number of auditory cells, including hair cells.

Further, the scope of the invention includes preventative treatments which arrest or slow progressive hearing loss conditions or which prophylactically protect subjects from experiencing a hearing loss condition. In one embodiment, the treatments of the invention are administered to an individual at risk for a hearing loss condition. For example, preventative treatments may be administered to aging subjects (e.g. subjects over 50, 55, 60, or 65 years of age), or subjects having genetic disposition for hearing loss. In some embodiments, the preventative treatments are administered to subjects that are imminently or potentially to be exposed to ototoxic agents, which are being exposed to ototoxic agents, or which have recently been exposed to ototoxic agents, for example, patients undergoing the administration of drugs having potential ototoxic side effects. Furthermore, in some embodiments, the preventative treatments of the invention are administered to subjects prior to, during, and/or shortly after exposure to excessive noise, for example workers (e.g. construction and pilots or airport workers), military personnel, and musicians or concertgoers.

The various treatments described herein encompass the administration of one or more therapeutic agents. The "therapeutic agent," as used herein may comprise a small molecule chemical species. It will be understood that the administration of specific small molecule agents described herein also includes the administration of analogs, variants, and derivatives of the disclosed compounds. The therapeutic agent may also comprise a biological species such as a polypeptide, antibody, nucleic acid, or hybrids thereof. Such administration of therapeutic agents described herein will be understood to comprise the administration of a therapeutically effective amount of the therapeutic agent, as known in the art.

It will be understood that such "administration," as used herein may encompass, oral, transdermal, intraperitoneal, subcutaneous, intravenous, or other administration routes, as appropriate for the particular therapeutic agent being administered. In one embodiment, the one or more agents is administered by infusion into the ear. Ear infusion, wherein the agent crosses the tympanic membrane and contacts auditory cells, such as hair cells, allows directed delivery to the ear and minimizes side effects that may occur with systemic administration. Such delivery of the agent may be accomplished by any transtympanic drug delivery methods known in the art. Exemplary transtympanic drug delivery methods include iontophoretic systems, for example, as described in U.S. Pat. No. 7,840,260, entitled, "Iontophoretic intra-tympanic drug delivery system," by Eply. Another potential transtympanic delivery system includes the use of membrane-permeating carriers, such as described in U.S. Pat. No. 8,822,410, entitled "Tympanic membrane permeating ear drops and uses thereof," by Simons. Another delivery system includes the use of hydrogels infused with therapeutic agents and chemical penetration enhances, for example, penta-block copolymer poloxamer 407-polybutylphosphoester gels as described in the article: "Treatment of otitis media by transtympanic delivery of antibiotics", by Rong Yang et al., Science Translational Medicine 8: 356 (2016). Additional transtympanic drug deliver methods include transtympanic injection or by surgical implantation of drug eluting pellets of like structures by tympanomeatal flap procedure.

It will be further understood that such administration includes the use of pharmaceutically acceptable carriers or excipients, as known in the art, for example to optimize or modulate the bioavailability or pharmacokinetics of the agent, facilitate delivery to target tissues, and/or preserve the therapeutic agent.

The various methods described herein are directed to the treatment of a hearing loss condition in an animal subject in need of such treatment. The animal subject may be of any species of animal, for example a human being, e.g. a human patient. The treatments of the invention may also be directed to non-human animals such as dogs, cats, rats, mice, horses, pigs, cows, and other species, for example, animals treated in a veterinary context or experimental test animals.

Biological Mechanisms.

As described in the Example below, the various embodiments of the invention are based on the discovery that the unfolded protein response, mediated by calcium fluxes, is implicated in the death of hair cells. Specifically, the inventor of the present disclosure has determined that drastic hearing loss occurs in mice wherein the gene TMTC4 has been knocked out. TMTC4 is a protein that modulates the action of calcium pump SERCA2b. When TMTC4 activity is reduced or ablated, SERCA2b activity is dysregulated, resulting in abnormal and excessive calcium fluxes from the endoplasmic reticulum. This aberrant calcium status initiates and enhances the unfolded protein response (UPR), leading to apoptosis-mediated cell death in hair cells and associated auditory cells. Accordingly, the treatments of the invention are directed to the various processes and pathways implicated in this discovery.

SERAC2b.

The Sarcoplasmic/Endoplasmic Reticulum Calcium Atpase 2b (SERAC2b) calcium pump is responsible for maintaining homeostatic calcium levels within the ER. Impairment or loss of SERCA2b activity in auditory cells triggers ER stress via over-activation of the unfolded protein response, leading to apoptosis and auditory cell death. Accordingly, in one aspect, the invention encompasses treatments directed to the modulation of SERCA2b activity. In one embodiment, the invention comprises treatments which enhance, increase, or restore SERCA2b activity, for example, in subjects having reduced (e.g. below normal) SERCA2b activity in auditory cells. In another embodiment, the invention includes treatments which stabilize SERCA2b activity, i.e. treatments which result in normal SERCA2b activity over time, as observed in normal subjects not having a hearing loss condition. For example, in one embodiment, the treatment reduces aberrant calcium fluxes into or out of the ER compartment. In one embodiment, the treatment results in the restoration of normal SERCA2b activity, e.g. SERCA2b activity which is within the normal range or which is closer to normal activity, compared to that untreated subjects. In one embodiment, the treatment results in normalized calcium status within the ER. In one embodiment, the treatment results in reduced or inhibited frequency and/or magnitude of aberrant calcium fluxes from the ER.

The scope of the invention also includes modulation of other SERCA calcium pumps.

Exemplary treatments include the administration of agents which modulate SERCA2b activity. In one embodiment, the invention comprises the administration of CDN1163, a known modulator of SERCA2b activity. Additional exemplary SERCA2b-enhancing agents include nitroxides such as 4-Hydroxy-2,2,6,6-tetramethylpiperidine-N-oxyl (tempol), ursodeoxycholic acid, and taurourosodeoxycholic acid. In another embodiment, the invention comprises the administration of an agent described in PCT Patent Application Publication Number WO/2010088450, by Zsebo and Dahl, entitled "Methods of treating diseases associated with the modulation of serca," for example wherein A and B are each, independently, H, halo, hydroxyl, alkoxy of 1-3 carbons, haloalkyl of 1-3 carbons, —CN, azido, or —NO$_2$; herein at least one of A and B is not H; E is H, F, Br, I, hydroxyl, alkoxy of 1-3 carbons, haloalkyl of 1-3 carbons, —CN, or azido; R$^3$ is H or alkyl of 1-3 carbons, Q is methyl, or R$^3$ and Q are joined together to form a 5-6 membered ring; and v, R$^2$ and G are selected from (i) and (ii) as follows: (i) is 0, R$^2$ is H or alkyl of 1-3 carbons; and G is H, halo, hydroxyl, alkoxy of 1-3 carbons, haloalkyl of 1-3 carbons, —CN, azido, or —NO$_2$, Or G is joined together with R$^2$ to form a 5-6 membered ring; and (ii) v is 1 to 3, R$^2$ is H or alkyl of 1-3 carbons; and G is H, halo, hydroxyl, alkoxy of 1-3 carbons, haloalkyl of 1-3 carbons, —CN, azido, or —NO$_2$. Further exemplary SERCA modulators include, for example, istaroxime, NOS, TUDCA and regucalcin, as described in PCT Patent Application Publication Number WO/2012129066, by Fu and Hotamisligil, entitled "New targets for treatment of ER stress."

TMTC4 Activity.

TMTC4, as demonstrated herein, binds to and modulates the activity of the SERCA2b calcium pump. In one embodiment, the invention comprises gene therapy treatments which augment reduced TMTC4 activity or which replace missing TMTC4 activity in individuals having TMTC4 deficit, for example in subjects, including newborns or juveniles, that have a genetic defect in TMTC4 expression or activity. In another embodiment, the invention comprises the administration of an agent comprising a TMTC4 agonist which enhances TMTC4 activity.

Calcium Homeostasis.

In another aspect, the invention encompasses the modulation of proteins implicated in the general regulation of Ca$^{2+}$ fluxes. Homeostatic regulation of Ca$^{2+}$ fluxes has a positive role in preventing ER stress and reduces the activation of cell death mechanisms, and thus may prevent damage to auditory cells. In one aspect, the invention is directed to the administration of agents known in the art which maintain or restore calcium homeostasis in cells and/or the ER compartment or which ameliorate the aberrant calcium fluxes that auditory cell death.

In one embodiment, the invention encompasses the administration of modulators of the plasma membrane calcium ATPase ATP2b. Exemplary ATP2b modulators include vanadate and eosin, and inhibitors in the caloxin family of peptides, for example as described in Chaudhary et al., "Caloxin: a novel plasma membrane Ca2+ pump inhibitor," Am J Physiol Cell Physiol. 2001 April; 280(4):C1027-30.

In one embodiment, the invention encompasses the administration of modulators of the inositol triphosphate receptor, or InsP3R. Exemplary InsP3R modulators include: adenophostin, 2-aminoethoxydiphenylborate; and 2-O-modified IP3 analogs that are partial agonists of IP3R, for example, the compounds described in Rossi et al., 2009, "Synthetic partial agonists reveal key steps in IP3 receptor activation," Nature Chem Bio 5:631-39.

In one embodiment, the invention encompasses the administration of modulators of the ryanodine receptor. The ryanodine receptors are intracellular calcium channels that are implicated in various processes involving the release of calcium ions from organelles. Exemplary modulators of the ryanodine receptor include 4-chloro-3-ethylphenol, trilfuoperazina, and 3,5-Di-t-Butylcatechol.

UPR Modulators.

The results presented herein demonstrate that hearing loss is linked to the death of auditory cells, including hair cells and/or supporting cells, wherein over-activation of the UPR, resulting from aberrant calcium fluxes, initiates apoptotic pathways and auditory cell death. In one aspect, the invention is directed to treatments that modulate UPR signaling molecules. Accordingly, the modulation of UPR response may be utilized to inhibit over-activation of the UPR in hair cells.

UPR responses are mediated via signaling molecules such as the inositol requiring enzyme 1 (IRE1) and the double stranded RNA-activated protein kinase-like ER kinase (PERK). IRE1 is a transmembrane protein of the ER which senses ER stress and initiates adaptive responses. However, prolonged IRE1 activity promotes apoptotic pathways and cell death. Likewise, PERK resides in the ER membrane and regulates the adaptive and apoptotic responses through complex regulatory pathways.

In one aspect, the invention encompasses the treatment of a hearing loss condition by administration of agents that (1) promote UPR adaptive responses; and/or (2) inhibit UPR-mediated apoptotic pathway. In one embodiment, the invention comprises the administration of an IRE1 modulator. In one embodiment, the IRE1 modulator is an IRE1 inhibitor. In one embodiment, the invention comprises the administration of a PERK modulator. In one embodiment, the PREK modulator is a PERK inhibitor. Exemplary IRE1 modulators include MKC-3946, STF-083010, 4μ8C, APY29, 1NM-PPI, KIRA3, and KIRA6. Exemplary PERK modulators include GSK2656157, GSK2606414, ISRIB (Integrated Stress Response inhibitor), or trans-N,N'-(cyclohexane-1,4-diyl) bis(2-(4-chlorophenoxy)acetamide), and sunitinib. In one embodiment, the invention comprises the administration of a Bip enhancing agent. In one embodiment, the Bip enhancing agent is 2-(3,4-Dihydroxyphenyl)-2-oxoethyl ester thiocyanic acid, also known as BiP protein Inducer X or BIX. In one embodiment, the invention comprises the administration of an ER stress response reducing agent. In one embodiment, the ER stress response reducing agent is 4-Phenylbutyric acid (4-PBA).

Screening Tools.

The invention further encompasses biological materials derived from TMTC4-impaired materials, including whole animals, and cells or tissue explants derived from such animals As used herein, "TMTC4 impaired biological material" means an organism, tissue explant, or cell wherein the transcription, translation or activity of the TMTC4 gene or protein has been substantially impaired or repressed therein relative to wild type controls, including by double knockout mutations, knockdown mutations, dominant negative mutants, and RNAi induced gene knockdown. In one embodiment, the invention comprises a TMTC4 impaired animal. In one embodiment, the invention comprises cells derived from a TMTC4 impaired animal, for example, cultured cells. In one embodiment, the cultured cells are fibroblast cells derived from skin cells. In another embodiment, the invention comprises a tissue explant derived from an TMTC4 impaired animal. In one embodiment, the explant is a cochlear explant. In one embodiment, the TMTC4 impaired material is or is derived from a mouse.

Figure 1:
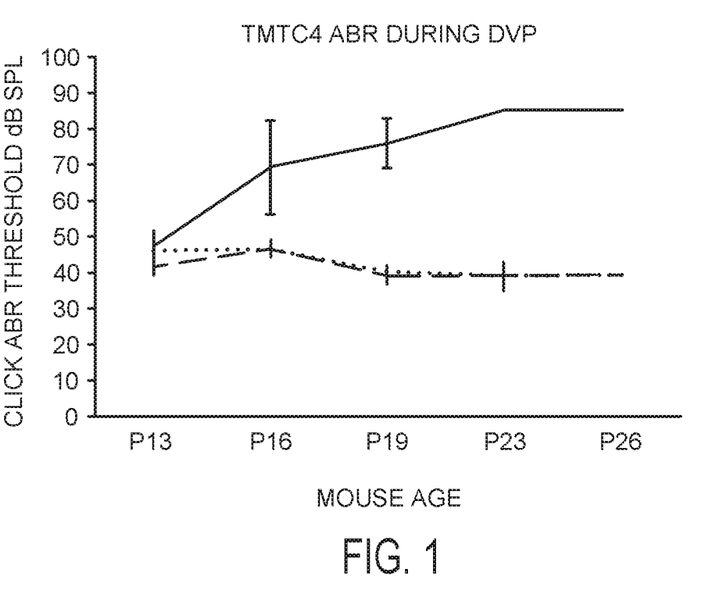
FIG. 1. Auditory brainstem response click threshold in mice at different developmental stages. Dotted line=wild type mice, Solid line=TMTC4 homozygous knockout mice, and Dashed line=heterozygous TMTC4+/- mice.

In one embodiment, the invention encompasses a screening method wherein TMTC4 impaired biological materials are used to identify novel therapeutic agents or to evaluate the efficacy of treatments which ameliorate a hearing loss condition, such as the death of hair cells, hearing loss symptoms, and other phenotypes associated with TMTC4 knockdown. For example, as depicted in Example 1, early hearing is intact in TMTC4 KO mice at developmental stage P13, with nearly complete hearing observed by about developmental stage P26, a period of about two weeks. Accordingly, the TMTC4 KO animals of the invention provide an ideal model for assessing treatments on short time scales. An exemplary screening method of the invention comprises the steps of: (1) administering a putative hearing loss treatment to TMTC4 impaired biological materials, comprising animals or materials derived therefrom; (2) assessing a measure of a hearing loss condition, for example, hearing ability, a symptom of hearing loss, or a process implicated in hearing loss (e.g. aberrant calcium flux, apoptotic UPR markers, hair cell death etc.); and (3) comparing the measure of the hearing loss condition observed in the treated biological materials against a control (e.g. similar untreated materials) to assess whether the putative hearing loss condition treatment was effective in preventing, ameliorating, or otherwise reducing the incidence or severity of the hearing loss condition in the treated materials. For example, in one embodiment, the animal is treated or materials are derived from the animal during the juvenile phase wherein hearing impairment develops in such animals. In one embodiment, the animal is a TMTC4 KO mouse and the treatment is administered during the juvenile development period of about P13 to about P26.

Example 1. TMTC4 Knockout Mice and the Role of Calcium Regulation and the UPR in Hair Cell Death TMTC4 Knockout Materials.

A TMTC4 heterozygous knockout (KO) mouse was generated by inserting a LacZ and Neomycin fusion construction in place of exons 1 through 3 of the TMTC4 gene. Heterogeneous TMTC4+/− mice were generated therefrom. Additionally, fibroblast cell cultures were generated from skin cells of the TMTC4 KO and heterogeneous TMTC4+/− mice.

Anatomical Analysis.

Analysis of the brains of the TMTC4 KO animals demonstrated that the corpus callosum, along with the anterior commissure and hippocampal commissure, the three main cerebral commissures in the brain were intact. Disrupted cochlear architecture was observed in the TMTC4 KO mice.

Hearing Ability.

Hearing ability (as measured by standard hearing threshold testing) was measured at various developmental stages in the homozygous TMTC4 KO mice, heterogeneous TMTC4+/− mice, and wild type mice. As depicted in FIG. 1, mice of all three genotypes had equivalent hearing ability at developmental stage P13. As mice developed, hearing ability remained stable in wild type and heterozygous TMTC4+/− mice, but progressively deteriorated in TMTC4 KO mice, to the point of total deafness by about stage P23. Characterization of hearing ability of P26 mice using pure tone testing, optoacoustic emission, and auditory brainstem response showed total loss of hearing in TMTC4 KO mice, even at 90 dB. This hearing loss was not confined to a particular frequency, being present with clicks and with tones varying from 8 to 32 kHz.

Hearing Loss in the TMTC4 KO Mice Appears to be Caused by Cell Death in the Cochlea.

Testing cochlear explants from KO and WT mice demonstrates broad-based loss of outer hair and inner hair cells. Hair cell abundance at the cochlear base was measured in mice of varying developmental stages by staining for myosin VIIa. TMTC4 KO mice demonstrated progressive hair cell loss, beginning at about developmental stage P10, with total loss of hair cells observed by developmental stage P45.

TMTC4 is Localized to the Endoplasmic Reticulum.

C-myc antibodies used to tag TMTC4 showed co-localization with the ER marker GRP94 in HEK cells. This co-localization was also shown in the brains of juvenile mice. This co-localization implicates over-activation of the ER stress response in cell death in the cochlea. Co-immunoprecipitation in HEK cells also showed TMTC4 to be in association with SERCA2b.

ER Stress is Over-Activated in TMTC4 KO Cells.

Fibroblast cells were generated from TMTC4 KO mice and wild type mice. One group of cells was treated with the SERCA2b inhibitor thapsigargin. The expression of UPR stress pathway genes spliced X-box binding protein 1 (S-XBP1), the molecular chaperone BiP, and the pro-apoptotic protein CHOP were measured by mRNA quantification. The expression of the UPR stress response markers was low and was about equal in untreated wild type and TMTC4 KO cells. However, in the thapsigargin treated cells, expression of the UPR stress response markers was substantially elevated in the TMTC4 KO cells compared to wild type cells.

In fibroblasts, the abundance of CHOP-expressing wild type and TMTC4 KO cells was quantified by CHOP antibody staining and flow cytometry. Increased activation of CHOP was observed in the TMTC4 KO cells, with 13% of wild type cells showing CHOP expression and 51% of TMTC4 KO cells having CHOP expression.

In fibroblasts treated with thapsigargin, the treated TMTC4 KO cells had substantially higher levels of CHOP and cleaved caspase 3 protein than treated wild type cells.

Figure 2:
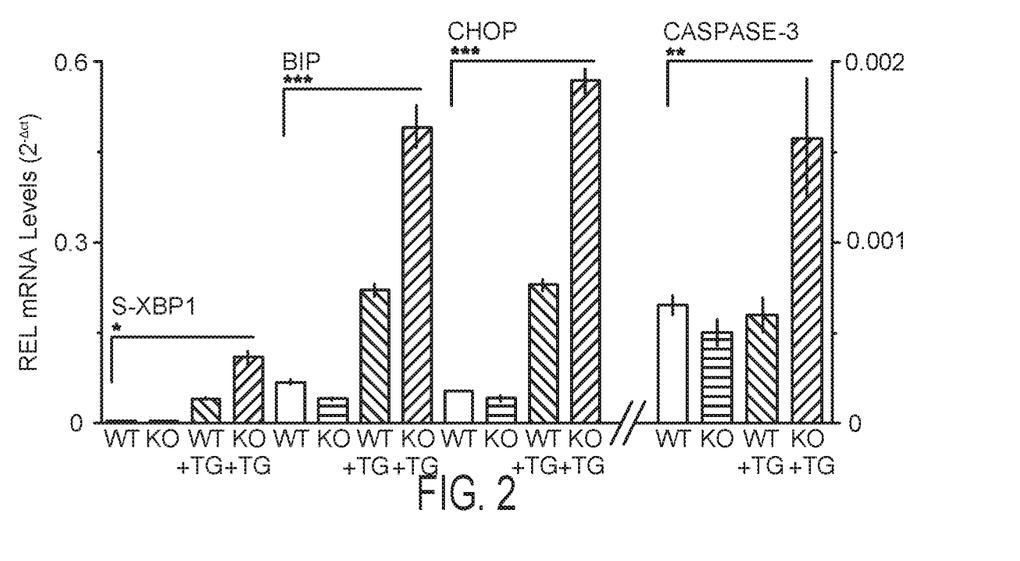
FIG. 2. SYBR Green measurement of qPCR product measuring RNA expression of spliced X-box binding protein 1 (S-XBP1), the molecular chaperone BiP, the pro-apoptotic protein CHOP, and Caspase 3 in cochlear explants from mice. WT=wild type and KO=TMTC4 knockout mice. +TG indicates explants treated with the SERCA2b inhibitor thapsigargin.

In another experiment, cochlear explants from TMTC4 KO and wild type mice were extracted. One group of explants was treated with the SERCA2b inhibitor thapsigargin. The expression of UPR stress pathway genes S-XBP1 BiP, CHOP, and the apoptotic gene Caspase 3 were measured by mRNA quantification (FIG. 2). In the untreated explants, the expression of the UPR stress response markers and of Caspase3 were about equal. However, in the thapsigargin treated explants, expression of the UPR stress response markers and of Caspase 3 was substantially elevated.

These results indicate over-activation of the ER stress pathway, and resulting apoptosis, in TMTC4 KO cells and in the cochlea of TMTC4 KO mice.

Calcium Fluxes and TMTC4.

Figure 3:
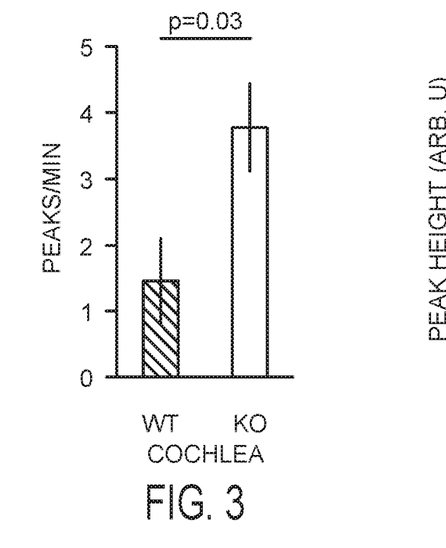
FIG. 3 depicts cytosolic calcium ion $Ca2^+$ peaks per minute in cochleae of wild type and TMTC4 KO mice.
Figure 4:
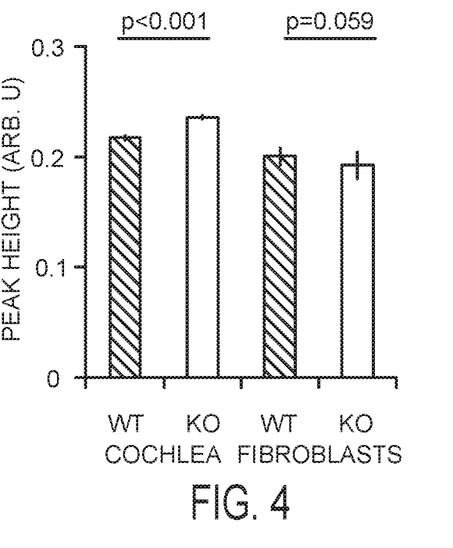
FIG. 4 depicts cytosolic $Ca2^+$ peak average peak height in arbitrary units for peaks in cochleae and fibroblasts.
Figure 5:
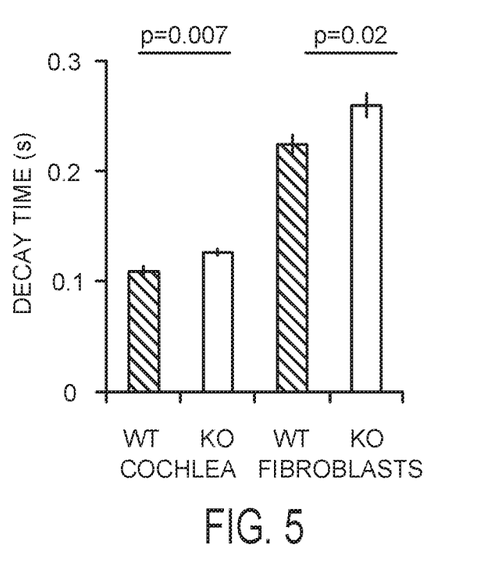
FIG. 5 depicts $Ca2^+$ peak average decay time for peaks in cochleae and fibroblasts.
Figure 6:
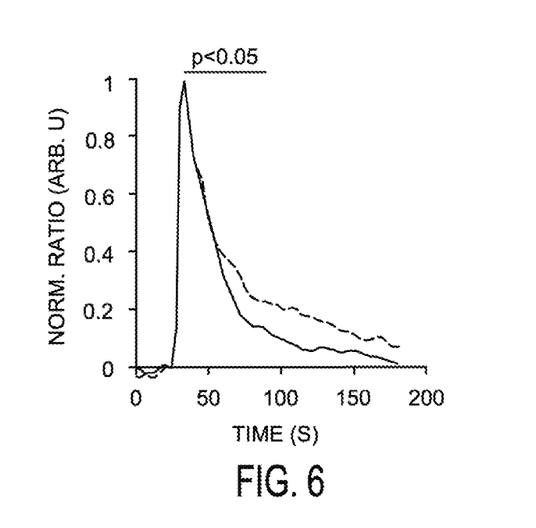
FIG. 6. depicts the aggregate peak time course for $Ca2^+$ peaks in cochleae. Solid line—wild type. Dotted line—TMTC4 KO.
Figure 7:
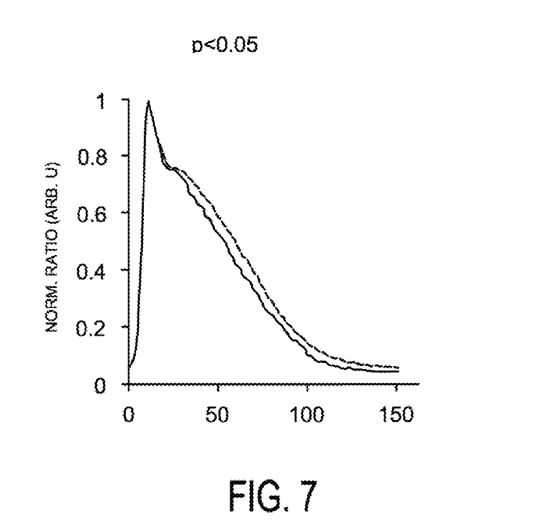
FIG. 7. depicts the aggregate peak time course for $Ca2^+$ peaks in fibroblasts. Solid line—wild type. Dotted line—TMTC4 KO.

In another experiment, the dynamics of calcium ion flux were measured in cells and cochlear explants. Cytosolic calcium ion concentration was measured in both fibroblasts and neonatal cochleae of wild type and TMTC4 knockout mice by FURA-2 ratiometric dye fluorescence during spontaneous (cochleae) and ATP-stimulated (fibroblasts) calcium ion peak activity. Peak frequency was greater in KO cochleae (FIG. 3). Peak height was slightly higher in KO cochleae, and indistinguishable in fibroblasts (FIG. 4). Decay time was significantly longer in both KO cochleae and fibroblasts (FIG. 5). Aggregate peak time course analysis of calcium ion peaks showed identical initial kinetics and subsequent significantly delayed return to baseline in the KO cochleae (FIG. 6) and fibroblasts (FIG. 7).

These experiments demonstrated that absence of TMTC4 leads to increased fluxes of calcium ions into the cytoplasm (and decreased concentration in the ER) and reduced ability to clear calcium ions from the cytoplasm. This would activate ER stress and resulting apoptosis. These findings demonstrate the relationship between calcium ion flux, ER stress and eventual hearing loss.

Calcium Gradients.

In one experiment, quantification of $Ca^{2+}$ was performed in intracellular compartments of fibroblasts by Mag-FURA-2 imaging. In wild type fibroblasts, an area of high $Ca^{2+}$ concentration in the perinuclear region corresponding to the ER was observed. When treated for ten minutes with 1 micromolar ATP and 1 micromolar thapsigargin, the $Ca^{2+}$ concentration of the same perinuclear region was reduced to that observed in the surrounding cytosol. Quantification of the $Ca^{2+}$ gradient between ER and cytosol compartments in fibroblasts was also measured in both wild type and TMTC4 KO mice. The gradient was significantly reduced in the TMTC4 KO cells, being about 33% of that observed in wild type cells. This demonstrates that there is a significantly reduced Ca2+ gradient in KO cells consistent with baseline depletion of ER Ca2+ due to aberrant SERCA activity.

Noise Induction of UPR Apoptotic Pathways.

Figure 8:
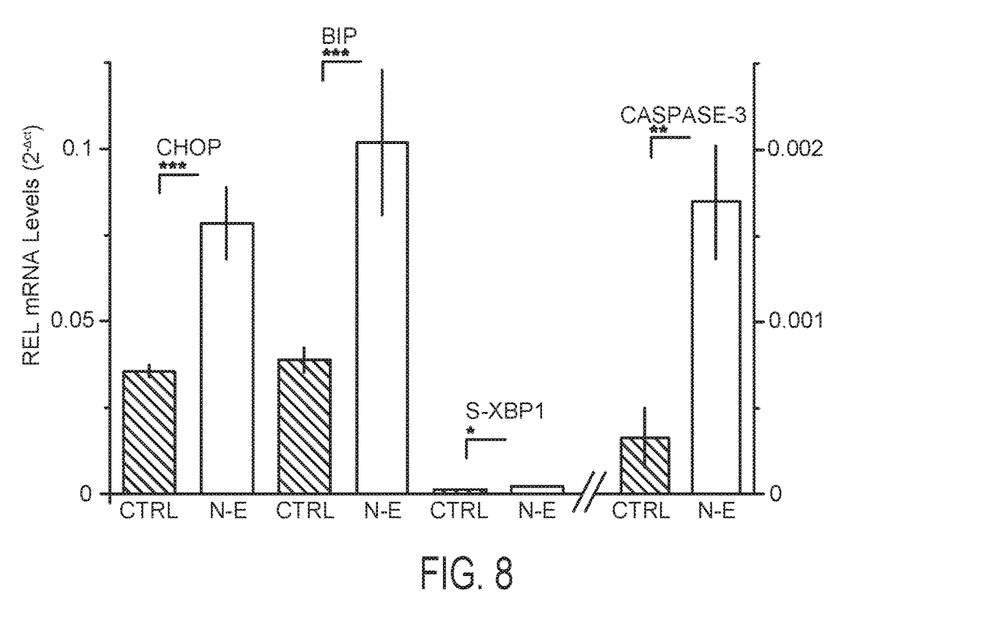
FIG. 8 depicts the quantification of CHOP, Bip, S-XBP1, and caspase 3 mRNA expression in cochleae of wild type mice exposed to sound at levels previously shown to cause hearing damage, two hours after such exposure. CTRL-untreated mice. N-E-noise exposed mice.

In another experiment, exposure of wild type mice to 120 db white noise across the 8-16 kH octave band for 120 minutes resulted in substantial loss of hearing across sound frequencies at day one following exposure, with some recovery in the days thereafter. Wild type mice were subjected to the same treatment and cochleae were subsequently removed and apoptotic ER response gene expression was assessed. Noise exposure caused a significant upregulation in CHOP, BiP, spliced X-box1, and Caspase 3 expression in cochleae (FIG. 8), demonstrating the role of UPR apoptotic response in the mechanism of hearing loss.

PERK Inhibitor Reduces UPR Induction Response.

In another experiment, HEK293T cells were pretreated with a control formulation or ISRIB, a PERK inhibitor, then exposed overnight to 1 micromolar thapsigargin for 2 hours. CHOP and ATF4 mRNA levels were then assessed by qPCR. A significant and substantial reduction in ATF4 and CHOP expression was observed in the cells treated with PERK inhibitor. This demonstrates the ability of PERK inhibitors to reduce UPR induction.

UPR Inhibition Preventatively Reduces Noise-Induced Hearing Loss.

Figure 9:
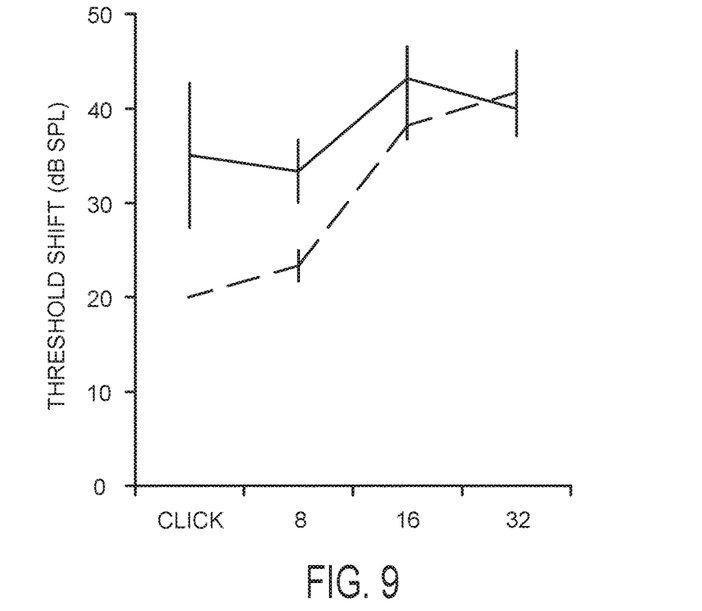
FIG. 9 depicts ABR threshold to click, 8 kHz, and 16 kHz stimuli in mice treated with ISRIB (dotted line, N=3)) compared with vehicle (solid line, N=3). All values are means with error bars indicating the standard error of the mean.

ISRIB was delivered to wild type mouse ear canals via intraperitoneal injection 4 hours before exposure to damaging noise, at 2.5 mg/kg. Subsequent hearing tests on treated mice showed that the ABR threshold to clicks at 8 kHz and 16 kHz was lower in treated mice than in untreated mice (FIG. 9). These results demonstrate that therapeutic intervention to reduce UPR apoptotic responses can preventatively protect animals from hearing loss associated with noise exposure.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of treating, in an animal, a hearing loss condition caused by unfolded protein response (UPR)-mediated cell death of auditory cells, comprising
    the administration of a pharmaceutically effective amount of an agent which inhibits protein kinase-like ER kinase (PERK)-mediated apoptosis of auditory cells;
    wherein the hearing loss condition is selected from the group consisting of noise-induced hearing loss, genetic or inherited hearing loss, and hearing loss experienced as a result of exposure to an ototoxic agent, wherein the ototoxic agent is cisplatin.

2. The method of claim 1, wherein
the auditory cells are hair cells.

3. The method of claim 1, wherein
the treatment is a therapeutic treatment administered to an animal afflicted with a hearing loss condition.

4. The method of claim 1, wherein
the treatment is a preventative treatment administered to an animal at risk of affliction with a hearing loss condition.

5. The method of claim 1, wherein
the agent is administered to the auditory cells of the ear.

6. The method of claim 1, wherein
the agent which inhibits PERK-mediated apoptosis of auditory cells is selected from the group consisting of Integrated Stress Response inhibitor (ISRIB), GSK2656157, GSK2606414, and sunitinib.

7. The method of claim 1, wherein the animal is a human.

8. The method of claim 3, wherein the animal is a human.

9. The method of claim 5, wherein the animal is a human.

10. The method of claim 6, wherein the animal is a human.

* * * * *